United States Patent [19]

Creaven

[11] Patent Number: 4,994,440
[45] Date of Patent: Feb. 19, 1991

[54] METHOD FOR THE TREATMENT OF RENAL CELL CARCINOMA

[76] Inventor: Patrick J. Creaven, 29 Woodhaven Rd., Amherst, N.Y. 14226

[21] Appl. No.: 310,256

[22] Filed: Feb. 13, 1989

[51] Int. Cl.$^5$ .............................................. A61K 37/02
[52] U.S. Cl. ........................................ 514/8; 530/322
[58] Field of Search ............................. 514/8; 530/322

[56] References Cited

U.S. PATENT DOCUMENTS

| | | |
|---|---|---|
| 4,548,923 | 10/1985 | Hartmann et al. . |
| 4,619,794 | 10/1986 | Hanser ................................. 264/4.1 |
| 4,738,843 | 4/1988 | Oguchi et al. . |
| 4,774,085 | 9/1988 | Fidler ................................. 424/85.5 |

FOREIGN PATENT DOCUMENTS 25495 of 0000 European Pat. Off. .

OTHER PUBLICATIONS

Creaven et al., Liposomes in the Therapy of Infectious Diseases and Cancer, pp. 297–303 (1989).
Comprehensive Textbook of Oncology, pp. 889–900, Williams and Wilkins, Baltimore (1986).
J. Of Urology, 117, pp. 272–275 (1977).
Cancer Principles & Practice of Oncology, 3rd Ed., (1989), p. 991.

*Primary Examiner*—Lester L. Lee
*Attorney, Agent, or Firm*—Irving M. Fishman; JoAnn Villamizar

[57] ABSTRACT

The present invention relates to a method for the treatment of renal cell carcinoma comprising administering to a warm blooded mammal in need thereof a therapeutically effective amount of N-acetylmuramyl-L-alanyl-D-isogutamin-yl-L-alanine-2-(1,2-dipalmitoyl-sn-glycro-3-hydroxyphosphoryloxy)ethylamide monosodium salt preferably encapsulated in a multilamellar liposomal composition comprising phosphatidylcholine and phosphatidylserine.

5 Claims, No Drawings

METHOD FOR THE TREATMENT OF RENAL CELL CARCINOMA

FIELD OF THE INVENTION

The present invention relates to the treatment of renal cell carcinoma by application of N-acetylmuramyl-L-alanyl-D-isoglutaminyl-L-alanine-2-(1,2-dipalmitoyl-sn-glycero-3-hydroxyphosphotyloxy) ethyl amide monosodium salt.

BACKGROUND OF THE INVENTION

Renal cell carcinoma has been referred to as renal cancer or adenocarcinoma of the kidney. There is no uniformly satisfactory treatment for metastatic adenocarcinoma of the kidney. This remains a major problem in therapy, since as many as 50% of patients have evidence of metastic disease.

Hormonal therapy has been employed in the treatment of advanced renal cell carcinoma based upon the estrogen dependency of renal tumors in an animal model. A recent review of hormone therapy showed a response rate of 2% among 415 patients. Hruskesky W. J. and Murphy GP: "Current Status of Therapy of Advanced Renal Carcinoma", *J. Surg. Oncol.*, Vol. 9, p277-288 (1977) cited in the *Comprehensive Textbook of Oncology*, Moossa, A. R. editor, Williams & Wilkins, Baltimore, Md. p889-900 (1986).

Surprisingly, N-acetylmuramyl-L-alanyl-D-isoglutaminyl-L-alanine-2-(1,2-dipalmitoyl-sn-glycero-3-hydroxyphosphoryloxy)ethylamide monosodium salt was found to reduce the size of lesions in a patient with renal cell carcinoma with multiple small pulmonary metastases.

Accordingly, the object of the present invention is the treatment of renal cell carcinoma.

DETAILED DESCRIPTION

The present invention relates to a method for the treatment of renal cell carcinoma comprising administering a therapeutically effective amount of N-acetylmuramyl-L-alanyl-D-isoglutaminyl-L-alanine-2-(1,2-dipalmitoyl-sn-glycero-3-hydroxyphosphorylox-y)ethylamide monosodium salt, preferably encapsulated in a multilammellar liposome composition comprising 1-palmitoyl-2-oleoyl-sn-glycero-3-phosphatidylcholine (synthetic phosphatidylcholine) and 1,2-dioleoyl-3-sn-phosphatidyl-L-serine monosodium salt (synthetic phosphatidylserine).

The present invention concerns in particular the treatment of man by using N-acetylmuramyl-L-alanyl-D-iso-glutaminyl-L-alanine-2-(1,2-dipalmitoyl-sn-glycero-3-hydroxyphosphoryloxy)ethylamide monosodium salt. In addition, it could also be applied to animals having renal cell carcinoma.

An effective amount is defined as diminishing the size of lesions in a patient with renal cell carcinoma with multiple small pulmonary metastases.

In order to achieve this effect N-acetyl-muramyl-L-alanyl-D-isoglutaminyl-L-alanine-2-(1,2-dipalmitoyl-sn-glycero-3-hydroxyphosphoryloxy)ethylamide monosodium salt is administered, preferably intravenously, in doses from about 0.01 mg/m$^2$ up to about 4 mg/m$^2$ either by one or two weekly injections.

The dosage has, of course, to be adjusted to the individual weight and general condition of the patient to be treated, and is finally dependent upon the judgement of the physician.

Pharmaceutical compositions for the treatment of renal cell carcinoma by reducing lesions comprise an effective amount of N-acetyl-muramyl-L-alanyl-D-isoglytaminyl-L-ala-nine-2-(1,2-dipalmitoyl-sn-glycero-3-hydroxyphosphoryloxy)ethylamide monosodium salt, preferably encapsulated in a multilamellar liposome composition comprising synthetic phosphatidylcholine and synthetic phosphatidylserine in a weight ratio of 7:3; i.e. an amount of about 2.5 mg up to about 1000 mg lipid.

In general, the pharmaceutical preparation contains an effective amount of the active ingredient, preferably encapsulated as set forth hereinabove, together or in admixture with inorganic or organic, solid or liquid, pharmaceutically acceptable carriers which are suitable preferably for parenteral administration.

The active ingredient of the present invention (N-acetylmuramyl-L-alanyl-D-isoglutaminyl-L-alanine-2-(1,2-dipalmitoyl-sn-glycero-3-hydroxyphosphoryloxy)ethylamide monosodium salt) is preferably used in the form of preparations for parenteral, for example subcutaneous, intramuscular or intravenous, administration. Such preparations are preferably isotonic aqueous liposomal suspensions which can be prepared before use, for example, from lyophilized preparations which contain the active ingredient together with a pharmaceutically acceptable carrier. The pharmaceutical preparations may be sterilized and/or contain adjuncts, for example preservatives, stabilizers, wetting agents and/or emulsifiers, solubilizers, salts for regulating osmotic pressure and/or buffers. The present pharmaceutical preparations, which may, if desired, contain further pharmacologically valuable substances, are produced in a manner known per se, for example by means of conventional dissolving or lyophilising processes, and contain from about 0.1% to 100%, preferably 1% to about 20%, and is the case of lyophilisates up to 100% of the active ingredient.

The active ingredient of the present invention is preferably encapsulated in a multilamellar liposome. Liposomes are aqueous dispersions of lipid arranged as spherical structures of a phospholipid bilayer enclosing a water compartment. The basic structure of liposomes is, therefore, similar to the structure of a natural cell, i.e. the cell membrane and the cytoplasm. Multilamellar liposomes have a diameter of about 0.5-10 $\mu$m and more than one membrane per liposome. The encapsulated active ingredient of the present invention in a multilamellar liposome preferably exhibits the following characteristics:

the average size of the liposomes is about 2.5 um
the liposome preparation is homogeneous
the procedure for preparation of the liposomal composition from the lyophilisate is established by measuring the size distribution of the liposome preparation using variable hydration times, shaking times or shaking speeds.

In order to be sure that the liposome suspension will have the desired liposome size distribution, the liposome suspension can be prepared by mechanically shaking with a Vortex mixer at a dial setting of 7 or by hand-shaking for one minute.

The foregoing pharmaceutical preparations can be marketed in the form of dry preparations and can be used in the form of an aqueous liposomal dispersion in a carrier liquid buffered to pH 7.0-7.8.

The pharmaceutical preparations according to the invention are manufactured for example, as follows:

(a) a homogeneous mixture comprising synthetic, phosphatidylcholine and phosphatidylserine and the active ingredient is manufactured and, for the manufacture of liposomes, the resulting homogeneous mixture is dispersed in an aqueous phase.

The homogeneous mixture is manufactured, for example, by film formation or preferably by lyophilisate formation.

Suitable solvents for the manufacture of the liposomal mixture by film formation are, for example, low-boiling and low-melting (below 0° C.), unsubstituted or substituted, for example halogenated, aliphatic or cycloaliphatic hydrocarbons, for example n-hexane, cyclohexane, methylene chloride or chloroform, alcohols, for example methanol, lower alkanecarboxylic acid esters, for example ethyl acetate, or ethers, for example diethyl ether, or mixtures of these solvents. The solvent is removed in vacuo, preferably under a high vacuum, or by blowing off with an inert gas, for example nitrogen.

The lyophilisate formation is carried out by lyophilising a solution of the phospholipids and the active ingredient to be encapsulated. Suitable solvents are solid during freeze-drying, for example at the temperature of a methanol-, ethanol- or acetone-dry ice mixture, together with the lipid components and the inclusion compounds, and are, for example, organic solvents having a melting point higher than 0° C., for example glacial acetic acid, benzene or dioxan, especially tert.-butanol.

A liposomal mixture can also be manufactured by spray-drying a solution of the phospholipids and the active ingredient in an organic solvent, for example chloroform. The liposomal mixture is obtained in the form of a powder.

An approximate mixing ratio of synthetic phosphatidylserine to synthetic phosphatidylcholine is from approximately 10:90 to approximately 50:50 w/w%, especially 30:70 w/w%, and is suitable for the manufacture of the liposomal mixture. The approximate mixing ratio of the active ingredient to the total amount of lipids is approximately from 0.001 to 1.0:1.0, preferably from 0.005 to 0.1:1.0 mol.

Dispersion is effected, for example, by shaking (for example Vortex mixer) or stirring the aqueous phase to which has been added the previously manufactured liposomal mixture of the synthetic phospholipids and the active ingredient. The formation of multilamellar liposomes, takes place spontaneously (spontaneous vesiculation), that is to say without the additional supply of external energy and at high speed.

Approximately from 0.1 to 50% by weight, preferably from 2 to 20% by weight (in relation to the total weight of the aqueous dispersion) of the homogeneous mixture can be dispersed in the aqueous phase.

Acidically or basically reacting aqueous dispersions are buffered to pH 7.0–7.8, preferably pH 7.2–7.4. Dispersion is preferably carried out in an aqueous phase that has already been buffered to that pH value.

The manufacture of the pharmaceutical compositions according to the invention in the form of aqueous liposome mixtures can also be carried out according to any of the other processes that have become known hitherto for the manufacture of liposomes, for example in customary manner by treating the aqueous dispersion contaig the phospholipids and the active ingredient with ultrasonic waves, or by infusion methods or reverse-phase evaporation.

Dispersion is carried out at temperatures below approximately 36° C., preferably at room temperature. If the thermal sensitivity of the compounds to be encapsulated demands, the process is carried out while cooling and optionally under an inert gas atmosphere, for example a nitrogen or argon atmosphere. The resulting liposomal dispersions are stable for a very long period (up to several weeks or months) in an aqueous phase. Pharmaceutical compositions in the form of aqueous liposome dispersions can, optionally after the addition of stabilisers, for example mannitol or lactose, be rendered storage-stable by freeze-drying.

The completed formation of liposomes and their content in the aqueous phase can be detected in a manner known per se using various physical measuring methods, for example with freeze fracture samples and thin sections in an electron microscope or by X-ray diffraction, by dynamic light scattering, by mass determination of the filtrate in an analytical ultracentrifuge and especially by spectroscopy, for example in the nuclear resonance spectrum ($^1H$, $^{13}C$ and $^{31}P$).

The buffer solutions used, having a pH of 7.0 to 7.8, are preferably sterile phosphate buffer solutions based on dihydrogen/hydrogen phosphate which can be manufactured, for example, in accordance with the instructions given in Hagers Handbuch der Pharmazeutischen Praxis, Springer Verlag, Volume 1, pages 357–359. Use is made especially of sterile isotonic calcium-free buffer solution having a pH of 7.2 (Dulbecco).

The following Examples illustrate the invention without limiting it. Temperatures are given in degrees Centigrade.

EXAMPLE 1

586 mg of sterile tert.-butanol, 0.1 mg of N-acetyl-muramyl-L-alanyl-D-isoglutaminyl-L-alanine-2-(1,2-di-palmitoyl-sn-glycero-3-hydroxyphosphoryloxy)ethylamide monosodium salt, 75 mg of 1,2-dioleoyl-3-sn-phosphatidyl-L-serine monosodium salt and 175 mg of 1-palmitoyl-2-oleo-yl-sn-glycero-3-phosphatidylcholine are dissolved in a round-bottomed flask. The solution is sterile-filtered over Acrodisc ® ($2.0 \times 10^{-7}$m) filter, introduced into a sterile phial and frozen at −45°. The phial is dried in vacuo until a temperature of 25° is reached, and sealed under an argon atmosphere.

Before use, 2.5 ml of sterile, calcium-free, phosphate-buffered (pH 7.2–7.4) saline solution (Dulbecco) are added to this dry preparation (lyophilisate) at room temperature, using a sterile syringe, and the phial is shaken for one minute in a standardised laboratory shaking apparatus (Vortex, stage 6). The resulting liposome dispersion is storable at 4° and is suitable for parenteral (i.v.) administration.

EXAMPLE 2 586 mg of sterile tert.-butanol, 0.1 mg of N-acetyl-muramyl-L-alanyl-D-isoglutaminyl-L-alanine-2-(1,2-dipalmito-yl-sn-glycero-3-hydroxyphosphoryloxy)ethylamide monosodium salt (manufactured according to European Patent Specification 25 495), 75 mg 1,2-dioleoyl-3-sn-phosphatid-yl-L-serine monosodium salt and 175 mg of 1-palmitoyl-2-oleoyl-sn-glycero-3-phosphatidylcholine are dissolved in a round-bottomed flask. The solution is sterile-filtered over Acrodisc ® ($2.0 \times 10^{-7}$m) filter and introduced into a sterile phial. The phial is rotated at 150 rpm and the solvent is removed by blowing in a stream, of purified nitrogen that has been filtered under a pressure of 1 bar, thereby producing a film. The phial is sealed under an argon protecting-gas atmosphere.

Before use, 2.5 ml of sterile, calcium-free, phosphate-buffered (pH 7.2–7.4) saline solution (Dulbecco) are added at room temperature, using a sterile syringe, to the film that has been manufactured, and the phial is shaken for ten minutes in a standardised laboratory shaking apparatus (Vortex, stage 6). The resulting liposome dispersion is storable at 4° and is suitable for parenteral (i.v.) administration.

EXAMPLE 3

Aqueous dispersions containing liposomes consisting of 75 mg (0.091 mmol) of 1,2-dioleoyl-3-sn-phosphatidyl-L-serine monosodium salt, 175 mg (0.231 mmol) of 1-palmito-yl-2-oleoyl-sn-glycero-3-phosphatidylcholine and from 0.1 mg up to 10 mg of N-acetylmuramyl-L-alanyl-D-isoglutaminyl-L-alanine-2-(1,2-dipalmitoyl-sn-glycero-3-hydroxyphosphoryl-oxy)-ethylamide monosodium salt can be manufactured in a manner analogous to that described in Example 2.

EXAMPLE 4

12 patients diagnosed as having metastatic renal cell carcinoma were given the liposomal composition in accordance with Example 2 at various dosage levels of the active ingredient by 1 hour infusion in 50 ml of isotonic saline through a safety filter twice a week for a total of 8 doses.

In the presence of stable disease or tumor response, a further course or courses is given as shown in Table 2.

TABLE 2

| PT# | STARTING DOSE | CUMULATIVE DOSE | NUMBER OF TREATMENTS | OUTCOME |
|---|---|---|---|---|
| 001 | .01 MG/M2 | .152 MG | 8 | Progressive Disease |
| 004 | .01 MG/M2 | 2.2264 MG | 33 | Stable then Progressive Disease |
| 007 | .05 MG/M2 | .8 MG | 8 | Progressive Disease |
| 008 | .05 MG/M2 | .8 MG | 8 | Progressive Disease |
| 014 | .2 MG/M2 | 6.4 MG | 9 | Progressive Disease |
| 015 | .4 MG/M2 | 8.16 MG | 17 | Stable then Progressive Disease |
| 018 | .4 MG/M2 | 6.4 MG | 8 | Progressive Disease |
| 020 | .8 MG/M2 | 12.8 MG | 8 | Progressive Disease |
| 021 | .8 MG/M2 | 11.2 MG | 8 | Progressive Disease |
| 024 | 1.2 MG/M2 | 48 MG | 24 | Stable then Complete Remission |
| 029 | 4.0 MG/M2 | 72 MG | 8 | Progressive Disease |
| 034 | 6.0 MG/M2 | 95.2 MG | 8 | Unknown |

(1) Complete Remission - Complete disappearance of all measurable disease for a minimum of 4 weeks.
(2) Partial Remission - A 50% or greater reduction in the sum of the product of the perpendicular diameters of each measured lesion for a minimum of 4 weeks without any increase in size of a lesion or new lesion.
(3) Progressive Disease - A 25–50% or greater increase in the sum of the product of the perpendicular diameters of a measurable disease or the appearance of any new lesions.
(4) Stable Disease - A response less than Partial Remission without progressive disease for a minimum of 4 weeks.

What is claimed is:

1. A method for the treatment of renal cell carcinoma comprising administering to a warm blooded mammal in need thereof a therapeutically effective amount of N-acetyl-muramyl-L-alanyl-D-isoglutaminyl-L-alanine-2-(1,2-di-palmitoyl-sn-glycero-3-hydroxyphosphoryloxy)ethylamide monosodium salt.

2. A method according to claim 1 wherein said N-acetylmuramyl-L-alanyl-D-isoglutaminyl-L-alanine-2-L-(1,2-dipalmitoyl-sn-glycero-3-hydroxyphosphoryloxy)ethylamide monosodium salt is encapsulated in a multilamellar liposome comprising synthetic phosphatidylcholine and synthetic phosphatidylserine in a molar ratio of 7:3.

3. A method according to claim 1 wherein said N-acetylmuramyl-L-alanyl-D-isoglutaminyl-L-alanine-2-(1,2-dipalmitoyl-sn-glycero-3-hydroxyphosphoryloxy)ethylamide monosodium salt is administered in an amount of about 0.01 mg/m² to about 4 mg/m² once or twice weekly.

4. A method according to claim 1 wherein said N-acetyl muramyl-L-alanyl-D-isoglutaminyl-L-alanine-2-(1,2-di-palmitoyl-sn-glycero-3-hydroxyphosphoryloxy)ethylamide monosodium salt is intravenously infused.

5. A method according to claim 1 wherein said mammal is a human.

* * * * *